(12) United States Patent
Wang et al.

(10) Patent No.: US 7,875,457 B2
(45) Date of Patent: Jan. 25, 2011

(54) ERASABLE TAGGANT DISTRIBUTION CHANNEL VALIDATION METHOD AND SYSTEM

(75) Inventors: Xiaomei Wang, Winchester, MA (US); Dale C. Flanders, Lexington, MA (US); Petros Kotidis, Framingham, MA (US); Christopher C. Cook, Bedford, MA (US)

(73) Assignee: Axsun Technologies, Inc., Billerica, MA (US)

( * ) Notice: Subject to any disclaimer, the term of this patent is extended or adjusted under 35 U.S.C. 154(b) by 1622 days.

(21) Appl. No.: 11/129,660

(22) Filed: May 12, 2005

(65) Prior Publication Data

US 2005/0255599 A1    Nov. 17, 2005

Related U.S. Application Data

(60) Provisional application No. 60/570,281, filed on May 12, 2004.

(51) Int. Cl.
*G01N 37/00* (2006.01)
(52) U.S. Cl. .............. 436/56; 235/385; 235/462.09
(58) Field of Classification Search ............... 436/56; 235/385, 462.09
See application file for complete search history.

(56) References Cited

U.S. PATENT DOCUMENTS

| | | | |
|---|---|---|---|
| 5,290,066 A | | 3/1994 | Mody |
| 5,401,059 A | | 3/1995 | Ferrario |
| 5,451,505 A | * | 9/1995 | Dollinger .................. 435/6 |
| 5,525,969 A | * | 6/1996 | LaDue ................. 340/573.4 |
| 6,165,609 A | | 12/2000 | Curatolo |
| 6,544,925 B1 | * | 4/2003 | Prusik et al. ............. 503/201 |
| 6,610,351 B2 | * | 8/2003 | Shchegolikhin et al. ........ 427/7 |
| 2002/0025490 A1 | | 2/2002 | Shchegolikhin et al. |
| 2003/0184082 A1 | | 10/2003 | Bilble et al. |
| 2005/0109984 A1 | * | 5/2005 | Potyrailo et al. ....... 252/299.01 |

(Continued)

FOREIGN PATENT DOCUMENTS

DE    10 2004 016 249 A1    10/2005

(Continued)

OTHER PUBLICATIONS

International Preliminary Report on Patentability from International Application No. PCT/US2005/016888, filed on May 12, 2005.

*Primary Examiner*—Jill Warden
*Assistant Examiner*—Dwan A Gerido
(74) *Attorney, Agent, or Firm*—Houston Eliseeva, LLP

(57) ABSTRACT

To address counterfeit problems, for example, we propose a secure, flexible, and cost-effective authentication solution that can be integrated into conventional distribution logistic systems. The proposed solution for product authentication and distribution channel validation comprises three major components: 1) machine-readable Raman-active chemical taggant; 2) a taggant reader; and 3) a taggant eraser. The proposed solution is to control and validate the distribution channel by authenticating the origin of products. Authentication is accomplished by verification of distinct taggants associated with the articles, such as on its label, along with other product distribution information in optical, spatial-encoding indicia, such as a barcode. The taggant information is used to identify, validate, and distinguish the origin of the source of the articles, such as goods or products. The taggant material is thereafter rendered unreadable by modifying the taggants to make obtaining the information unfeasible, thereby controlling the taggants' lifecycle.

15 Claims, 3 Drawing Sheets

U.S. PATENT DOCUMENTS

| | | |
|---|---|---|
| 2005/0112768 A1 | 5/2005 | Evans et al. |
| 2005/0127176 A1* | 6/2005 | Dickinson et al. ........... 235/385 |
| 2006/0152706 A1 | 7/2006 | Butland |

FOREIGN PATENT DOCUMENTS

| | | |
|---|---|---|
| DE | 60208901 T2 | 7/2006 |
| GB | 2 383 776 A | 7/2003 |
| WO | 96/39302 A2 | 12/1996 |
| WO | WO 96/39302 A | 12/1996 |
| WO | 02/085543 A1 | 10/2002 |
| WO | WO/ 03/104851 A2 | 12/2003 |
| WO | 2004/017250 A2 | 2/2004 |
| WO | 2004/072868 A1 | 8/2004 |
| WO | 2005/055156 A2 | 6/2005 |

* cited by examiner

ERASABLE TAGGANT DISTRIBUTION CHANNEL VALIDATION METHOD AND SYSTEM

RELATED APPLICATIONS

This application claims the benefit under 35 USC 119(e) of Provisional application No. 60/570,281, filed May 12, 2004 which is incorporated herein by reference in its entirety.

BACKGROUND OF THE INVENTION

Raman spectroscopy is similar to infrared (IR), including near infrared (NIR), spectroscopy but has several advantages. The Raman effect is highly sensitive to slight differences in chemical composition and crystallographic structure. This characteristic makes it very useful for the investigation of illegal drugs as it enables distinguishing between legal and illicit compounds, even when the compounds have similar elemental compositions. Also, when using IR spectroscopy on aqueous samples, a large proportion of the vibrational spectrum can be masked by the intense water signal. In contrast, with Raman spectroscopy, aqueous samples can be more readily analyzed since the Raman signature from water is relatively weak. And, because of the poor water signature, Raman spectroscopy is often useful when analyzing biological and inorganic systems, and in studies dealing with water pollution problems.

Raman scattering may be regarded as an inelastic collision of an incident photon with a molecule. The photon may be scattered elastically, that is without any change in its wavelength, and this is known as Rayleigh scattering. Conversely the photon may be scattered inelastically resulting in the Raman effect.

Taggant technology is most commonly used for detection and source identification. In one common detection application, chemical or physical markers are added to explosives during their manufacture. Then, detection of this taggant can then be used to indicate the presence of the explosive during airport screening, for example. In an identification application, the taggants are engineered to survive the explosion so that they can be used to identify the source of the explosives as part of a forensic operation in which a unique Raman spectra for taggants are associated with the batch of explosives containing the taggants.

Taggant technology is being proposed for many new commercial applications. It can be used to manage supply chains for articles to ensure that the articles originated from the specified source and are not counterfeit or gray-market. Markets include aircraft parts, stamps, negotiable financial instruments (such as currency, checks, stamps, vouchers, stock certificates, bonds, script, food stamps), identification and travel documents (such as passports, ID cards, visas, health cards,), identification labels (apparel industry), packaging or seals on items such as CDs, DVDs and software. Of particular concern is counterfeiting in the pharmaceutical industry. This has raised special concerns from the healthcare and pharmaceutical industries, as well as Food and Drug Administration (FDA) regulators. Instead of simple economic loss, manufacturers' and distributors' reputations, counterfeit drugs put patient lives at risk.

A number of taggant technologies exist, such an NIR and fluorescence taggants. One of the most promising taggant technologies for counterfeit prevention applications are Raman taggants. These are typically organic, monomeric or polymeric compositions that have Raman active components, such as azo, azomethine or polycyclic chromophores, polydiacetylenes colloids or other nano scale metal particles, or phtalocyanines. Information is encoded by the taggants relating or associating the unique Raman spectra of the taggants to information about a given article. The taggants' information is obtained by irradiating the taggants with light, such as from a laser, and then detecting the spectral response in the Raman wavelengths. The detected spectrum is then matched against spectra in library to identify the taggants and thereby derive the information about the article associated with the identify taggants.

SUMMARY OF THE INVENTION

To address the problems such as counterfeiting, we propose a secure, flexible, and cost-effective authentication solution that can be seamlessly integrated into conventional distribution logistic systems. The proposed solution for product authentication and distribution channel validation comprises three major components: 1) machine-readable, preferably Raman-active, chemical taggants and possibly an associated tagging device for associating the taggants with the articles of interest; 2) a taggant reader; and 3) an eraser for the taggants. An inventory control system is also preferably included as part of the system to allow for the centralized analysis, reporting, and recording of the information from the reader.

The proposed method is to control and validate the articles in the distribution channel by authenticating the origin of the articles. Authentication is accomplished by verification of distinct taggants associated with the article, such as on its label, along with other product distribution information usually in optical, spatial-encoded indicia, such as a barcode. The taggants, usually made of complex, long-chain polymers, produce distinct, usually complex spectral fingerprints when interrogated by the reader. The chemical fingerprint is associated with information that is used to identify, validate and distinguish the origin of the source of the articles, such as goods or products, e.g., drugs or medicaments. Each supplier in the distribution chain has its own unique taggant materials for taggant labeling, in one example. The labels are typically applied to the packages or containers of the units to be supplied to the downstream customer—it is usually neither necessary nor desirable to apply the taggants to the article, such as the drug itself. As it is part of the distribution chain logistics, the authentication information should be integrated with the logistics data management system.

In general, according to one aspect, the invention features a taggant system. This system comprises taggant material that was associated with articles. The taggant material is usually taggants or taggants combined with a vehicle, binder, substrate, or medium holding the taggants.

The taggants represent information about the articles. Examples of articles include goods, goods in commerce, and tangibles representing services, for example. More specific examples include aircraft parts, stamps, negotiable financial instruments (such as currency, checks, stamps, vouchers, stock certificates, bonds, script, food stamps), identification and travel documents (such as passports, ID cards, visas, health cards,), identification labels (apparel industry), packaging or seals on items such as drugs or medicaments, CDs, DVDs and software.

A taggant reader is used to analyze the taggant material to determine the particular taggants and thereby determine the associated article information such as the information about the article that is associated with the unique Raman spectral fingerprint.

A taggant eraser is also provided to modify the taggant material to make subsequent identification of the taggants and thus determination of the information less feasible. Specifically, the chemical and/or physical structure of the taggants is preferably modified using the taggant eraser such that the original taggant spectum and thus the information is destroyed or nearly destroyed such that it would be difficult to obtain it or rendering the information less easily obtainable after modification by the eraser.

Preferably, the taggant reader comprises a radiation source for irradiating the taggant material and a spectrometer for determine a Raman spectral response of the taggant material. The taggant eraser preferably comprises a radiation source that heats the taggant material to induce chemical and/or physical changes to the taggant material to affect the information content of the taggant material, in one embodiment.

The taggant eraser can comprise the radiation source of the reader wherein a power projected to the taggant material by the radiation source is changed between an analysis mode for analyzing the taggant material and an erasure mode for modifying the taggant material.

In other embodiments, the taggant eraser comprises a radiation source that irradiates the taggant material with a different wavelength or a different spectral content than that used during the analysis mode.

In one embodiment, the taggant material is associated with indicia that contain spatially encoded information. One example of spatially encoded information is written text. Another example of indicia is machine readable spatial encoded information such as bar codes, including two dimensional bar codes.

One modification to make the system even more secure is to cover the taggant material or use a taggant binder material in which removal of the covering or exposure of the binder material induces modification of the taggant material, such as oxidation from exposure to the atmosphere or unfiltered light that makes determining the original spectral fingerprint less feasible.

In a current planned embodiment, the articles are medicaments such as pills and the taggant material is on a label for the pills, such as a bar code label identifying the type of pills.

In general, according to another aspect, the invention features a taggant tracking method. This comprises a first entity having taggant material associated with articles. The taggant material information about the articles. A second entity then receives the articles from the first entity. The second entity analyzes the associated taggant material to determine the information. After determining the information, the taggant material is modified to make determining the information less feasible in the future.

In a preferred embodiment, the second entity associates new taggant material with the articles, the new taggant material represents information about the articles and the second entity. This allows a third entity, upon receiving the articles from the second entity, to analyze the new taggant material to determine the information of the taggant material to thereby possibly validate the articles as genuine.

In general, according to another aspect, the invention features a label system. This label system has indicia having spatially encoded optically readable information and taggant material. In another aspect, the label system comprises taggant material and a covering over the taggant material. Preferably, removal of this covering induces modification to the taggant material that renders obtaining the original Raman spectrum of the taggant material less feasible.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
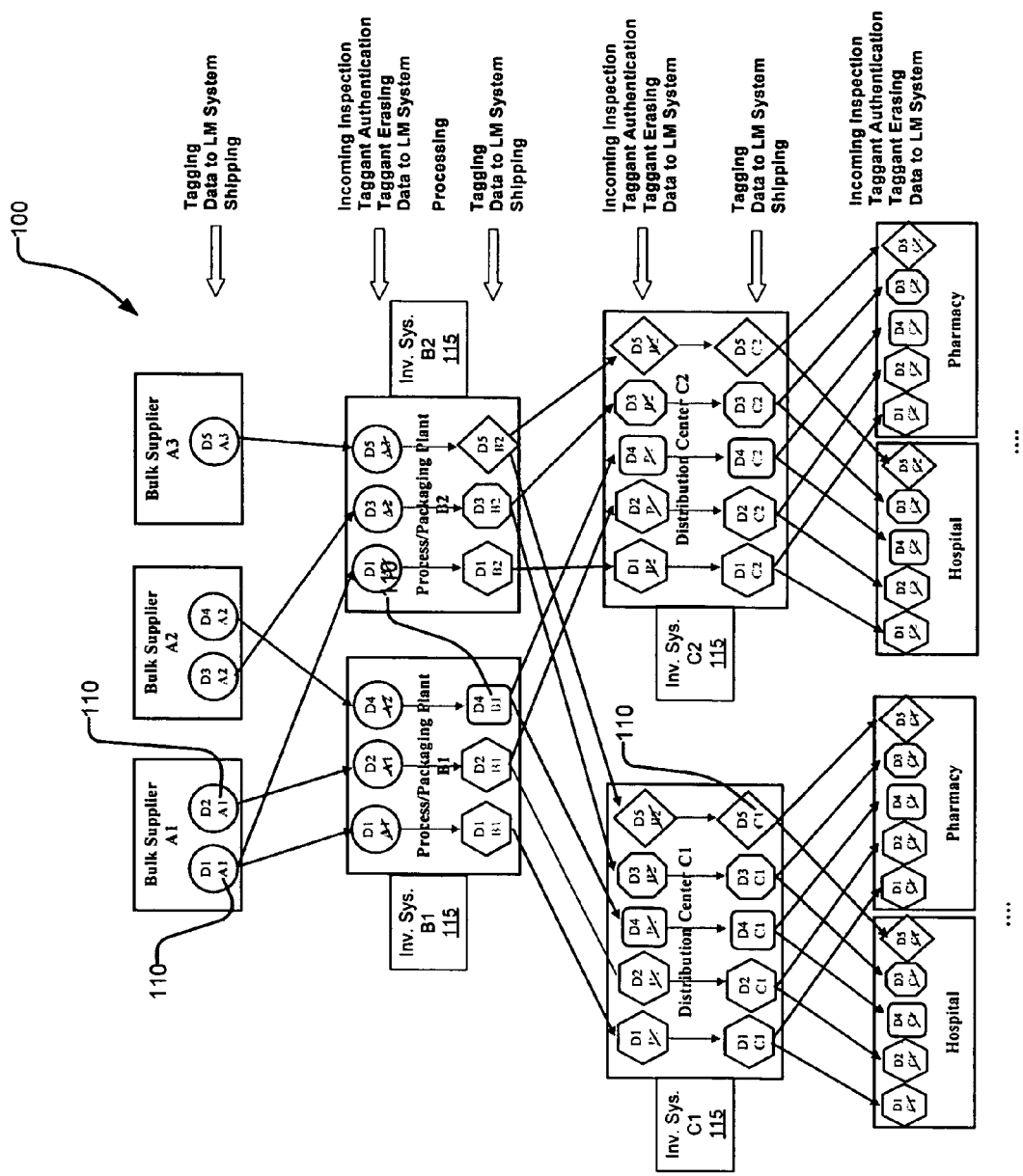
FIG. 1 shows an article tracking system and method according to the present invention.

FIG. 1 shows a taggant-based article tracking system for a supply chain, for example, which tracking system has been constructed according to the principles of the present invention.

Generally, in the illustrated system, during the incoming inspection by the down-stream customer, the taggants are interrogated and read with the reader to obtain information that is encoded in or represented by the taggants. The information usually concerns the origin of the articles passing through the supply chain. In one example, the information is used to verify the upstream supply or source of the articles.

In one example, the taggants are interrogated with a 980 nanometer semiconductor laser and read with a microelectromechanical system (MEMS) Fabry-Perot tunable filter spectrometer as described in U.S. patent application Ser. No. 10/967,075, filed on Oct. 15, 2004, entitled Integrated Raman Spectrometer System, by Xiaomei Wang, which is incorporated herein by this reference. The process of reading the taggants involves determining the Raman spectral response of the taggants and the comparing the response to a library of possible taggants to find a match.

Upon verification, the taggants are erased such that it is no longer feasible to obtain the source, inventory/article information from the taggants. This process can involve the permanent, complete destruction with the same reader or a separate eraser device. Alternatively, the process can involve the substantial destruction of the taggants such that obtaining the original taggant spectrum corresponding information is near impossible or at least very difficult, possibly requiring special laboratory analysis.

The erasure process is preferably accomplished by increasing the power or changing the wavelength of the reader's laser radiation source so that the taggants are heated to induce chemical and/or physical changes in the taggants or a material, such as binder or vehicle, carrying the taggants, to thereby destroy the taggants' unique spectral features or render obtaining the unique spectral feature difficult such as by rendering a taggant substrate, taggant carrier, binder material, and/or taggant coating material opaque to the wavelength used by the reader.

This feature of taggant erasure is significant—it is a security measure to prevent unauthorized subsequent use of the labels, containers, or packages. Once again, the incoming inspection verification data are transmitted to the inventory management system 115. After re-packaging, processing, or merely inventory counting, "customer B" becomes "supplier B" to down-stream "customer C". The goods leaving site B will be tagged with unique taggant B. This cycle is applied at each transaction point where necessary through the whole distribution channel: from the bulk supplier to the end-user.

The proposed system can be designed to fit each customer's special needs. For example, separate taggants that are product-specific can be applied to the units along with the supply chain authentication taggants. These taggants are for drug authentication only and would travel through the whole distribution channel 100 unaltered.

The proposed solution has several distinct advantages.

The design and manufacture of the Raman-active taggants is tailored to the security application. These taggants are usually special, complex, long-chain polymers, which cannot be obtained on the open market. There are a large number of molecule classes and mixtures that can be used for the taggant manufacturing. This allows a virtually unlimited variety of taggants for use. Reverse engineering of the taggants' chemical structure based on the observed spectrum is extremely difficult. For further security enhancement, unique taggants can be introduced as needed.

Security is also addressed at the reader and system levels. At the reader level, data processing and verification are preferably performed autonomously—only positive/negative authentication results are presented to the users and the information system. More importantly, this system controls the lifecycle of the taggants on the labels once they are in the distribution system by destroying the taggants at the end of designed transactions. This eliminates the possibility of empty containers, packages, or even labels being improperly or illegally reused for counterfeit drugs.

Simplicity, Flexibility and Compatibility

Compared with other authentication techniques such as direct characterization of pharmaceutical drugs themselves, the proposed solution is simpler, more manageable, and widely applicable. Another significant advantage of the proposed system is that the method of applying taggants to the labels or packages can be an inkjet-like printing process, compatible with the barcode generation methods currently utilized in inventory control. This extendibility and compatibility makes the adaptation of the proposed system relatively easy.

The system can also be made cost effective. With millions of products going through distribution channels, it is very important that the taggants be cost effective. Compared with other technologies such as radio frequency identification (RFID) or optically-shifted or optically-variable pigments, secure polymer based taggants are believed to offer significantly lower cost.

In more detail, FIG. 1 shows a series of bulk suppliers A1, A2, A3. Each of these bulk suppliers, for example, could be a drug producer or manufacturer producing drugs D1, D2, D3, D4 and D5.

In order to indicate that these drugs D1-D5 are from the respective manufactures/suppliers A1, A2, A3, they are each labeled with taggant material 110 that identifies or represents the corresponding bulk supplier A1, A2, A3.

Then, the drugs enter the supply chain 100. They are distributed to intermediate entities in the supply chain such as process/packaging plants B1/B2. As each of the drugs D1-D5 is received, the taggants A1-A3 of the bulk suppliers B1, B2 are then read and analyzed by the inventory management systems 115 for each of these process packaging plants B1, B2. The information represented by the taggants is determined and checked against the information in the inventory systems 115 concerning the articles in order to confirm that the drugs were received from the proper bulk suppliers and are not counterfeit. The taggant information is also preferably cross-checked against any other information such as information encoded in bar codes on the drug packaging.

In the preferred embodiment, these taggants, identifying the origin of the drugs A1, A2, A3, are then erased. Specifically, the taggants are chemically and/or physically modified such that obtaining the original spectral response and thus the encoded information of the taggants becomes less feasible, such as impossible, to obtain.

Each of the processing/packaging plants, B1, B2, then labels the drugs D1-D5 with their own taggants B1, B2 110. These taggants 110 are then read by the distribution centers C1, C2. The information represented by these taggants B1, B2 110 is then used by the inventory systems 115 of the distribution centers C1, C2 to confirm that the drugs came from the proper process/packaging plants. The taggants B1, B2 are then preferably destroyed at the distribution centers C1, C2.

New taggants C1, C2 110 are added to the drugs D1-D5 by the distribution centers C1, C2. These are then used by the entities near the end of the distribution chain, such as hospitals and pharmacies to confirm that the drugs are not counterfeit and are from the proper distribution center C1, C2, for those drugs.

Figure 2:
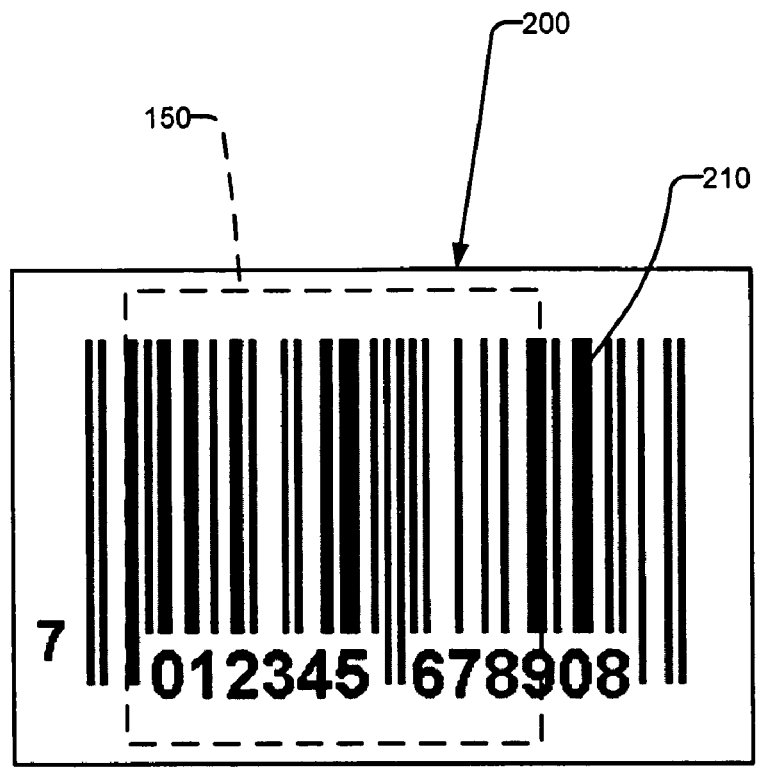
FIG. 2 is a front plan view of a label system according to the present invention.

FIG. 2 illustrates one example of a label for carrying the taggants of the supply chain 100.

Specifically, the label 200 in the preferred embodiment comprises indicia 210 that have spatially encoded information. Examples of spatially encoded information are human readable text and numbers. Alternatively, machine readable systems such as the illustrated bar codes 210 are used in other embodiments.

The spatially encoded information would include information such as type of drug and possibly its origin including date of manufacture. The label 200 preferably has another region such as region 150 that contains the taggants that represent the same or other information concerning the articles. In one example, the taggant material is distributed in a region of the label 150. Thus, the spatially encoded information 210 and the taggant information 150 can be obtained by one reader, interrogating the label 200 both in the optical wavelengths and by irradiating the label with the wavelengths required to obtain the Raman spectra for the taggants in region 150.

In another embodiment, the actual pigments used in the spatially encoded information 210 contain the taggants. Thus, the label is read both in the optical spectrum to obtain the spatially encoded information and in the Raman spectral wavelengths to obtain the Raman spectra. One further modification is to spatially encode the taggants such that different taggants are placed at different regions of the label 200. For example, the different lines of the bar code have different associated a taggants, in one example, with the different taggants' location encoding further information.

Figure 3:
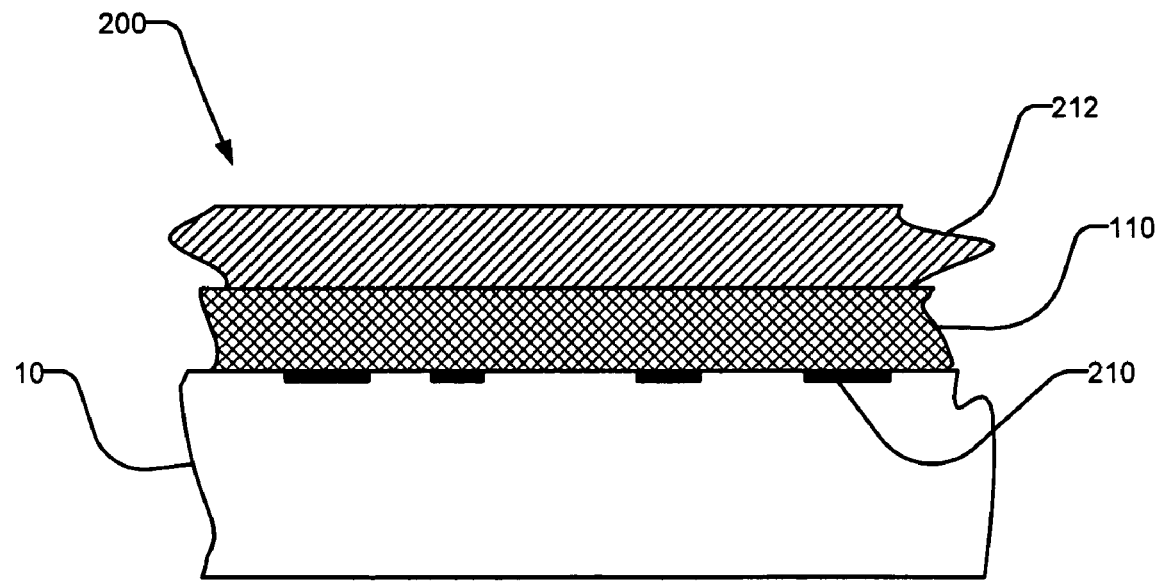
FIG. 3 is a side cross-section view of the inventive label system.

FIG. 3 is a cross-sectional view illustrating one embodiment of the label 200. Specifically, the label 200 comprises a substrate material 10 such as paper or adhesive-backed paper or plastic film material. On this substrate 10 are the regions of pigment 210 associated with the spatially encoded information such as the imprinted bar code. The illustrated example, the taggants are disposed as a material film layer over the substrate 210 and possibly over the regions of pigment for the spatially encoded information.

In one embodiment, the taggants are contained within an adhesive or glue vehicle or binder material to thereby form the taggant material layer 110.

In one embodiment, a covering 212 is provided for the taggants 110. This covering is used to protect the taggants 110 from interaction with or exposure to the atmosphere.

According to one aspect of the invention, removal of the cover 212 induces changes in the taggant material 110. In one example, the taggants are chemically reactive such that removal of the covering 212 exposes the taggants 110 to the atmosphere such that they react, changing their spectral response and thus destroying the information represented by the taggants. In another example, the taggant material vehicle, medium, or binder material of the taggants is chemically reactive to the atmosphere such that removal of the covering causes the binder material to react or otherwise change possibly making the binder material of the taggants 110 opaque to the wavelengths used for the taggant interrogation. In still another example, removal of a light filtering covering 212 exposes the taggant material to full spectrum light that induces the changes to the taggants' spectra. The result is that determining the taggant Raman spectrum and the information becomes infeasible with the removal of the covering 212.

Figure 4:
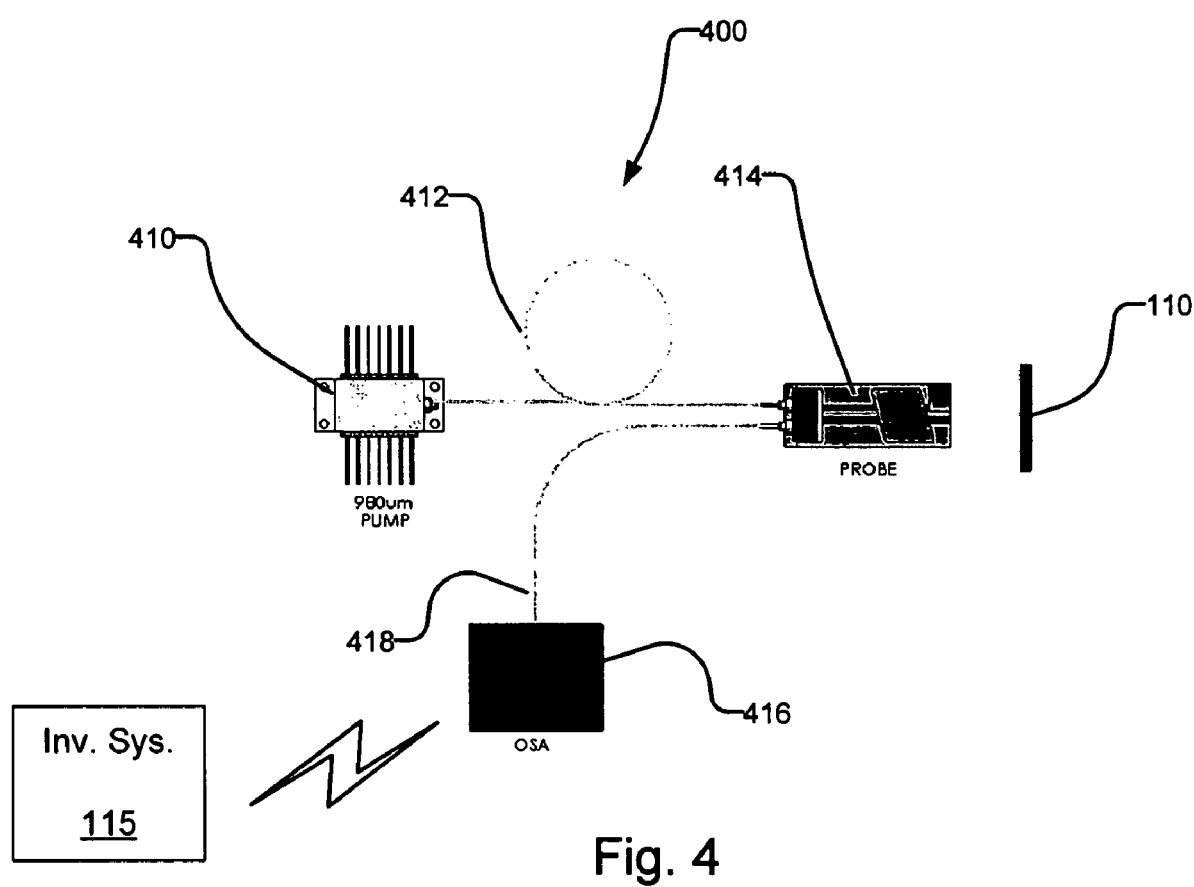
FIG. 4 is a schematic view of taggant reader/erasure system of the present invention.

FIG. 4 illustrates one example of a taggant reader/eraser 400. In this example, it comprises a semiconductor laser radiation source 410, such as an approximately 980 nanometer pump laser. In the illustrated embodiment, it is coupled by a length of optical fiber 412 to a probe head 414. This projects the laser radiation generated by the laser source to the taggant material 110. The probe 414 also captures the returning Raman spectra from the taggant material 110 and transfers it to an optical spectrum analyzer/controller 416. This is done in one example by a fiber optic link 418.

The optical spectrum analyzer/controller 416 determines the Raman spectra and then possibly either matches the spectrum to a library of spectra to determine the represented information encoded in the Raman spectra or passes the raw spectral information to the inventory system 115 of the entity via a radio-frequency communications link. There, the information is used to verify the origin, for example, of the articles with which the taggant material 110 is associated. A true/false signal is then returned to the controller 416.

In the preferred embodiment, the taggant material 110 is erased by increasing the power of the laser radiation source 410 to induce chemical and/or physical changes in the taggant material, such as to the taggants or a binder material or covering material, for example, of the taggant material. These changes make reading the taggant material and obtaining the information less feasible in the future.

Thus, when the controller 416 is in analysis mode, it analyzes the taggant material's spectral response, and when it is in an erasure mode, the controller modifies the taggant material.

In other embodiments, a radiation source irradiates the taggant material with a different wavelength or has a different spectral content during the erasure mode than that used during the analysis mode, in order to render the taggant material erased or unreadable.

While this invention has been particularly shown and described with references to preferred embodiments thereof, it will be understood by those skilled in the art that various changes in form and details may be made therein without departing from the scope of the invention encompassed by the appended claims.

What is claimed is:

1. A taggant tracking method comprising:
   a first entity having taggant material associated with articles, the taggant material representing information about the articles, the information being encoded in a spectral response of the taggant material;
   a second entity receiving the articles from the first entity;
   the second entity analyzing the taggant material to determine the information by determining a spectral response of the taggant material; and
   after determining the represented information, the second entity modifying the taggant material to change the spectral response of the taggant material with a radiation source that heats the taggant material to induce chemical and/or physical changes in the taggant material to affect an information content of the taggant material.

2. A method as claimed in claim 1, wherein the taggant material comprises long chain polymers.

3. A method as claimed in claim 1, wherein the radiation source is part of a reader, wherein a power projected to the taggant material by the radiation source is changed between an analysis mode for analyzing the taggant material and an erasure mode for modify the taggant material.

4. A method as claimed in claim 1, further comprising placing a covering over the taggant material, wherein removal of the covering induces modification to the taggant material that changes a spectral response of the taggant material.

5. A method as claimed in claim 1, further comprising:
   the second entity associating new taggant material with the articles, the taggant material representing information about the articles and the second entity;
   a third entity receiving the articles from the second entity; and
   the third entity analyzing the taggant material to determine the information of the new taggant material.

6. A method as claimed in claim 1, further comprising determining the information by using a taggant reader comprising:
   a radiation source for irradiating the taggant material; and
   a spectrometer for determining a spectral Raman response of the taggant material.

7. A method as claimed in claim 1, further comprising covering the taggant material, wherein removal of the covering induces modification to the taggant material that changes a spectral response of the taggant material.

8. A method as claimed in claim 1, wherein the articles are medicaments.

9. A method as claimed in claim 1, wherein the articles are pills and the taggant material is on a label for the pills.

10. A method as claimed in claim 1, further comprising an inventory control system for storing the information from the taggants.

11. A method as claimed in claim 1, wherein the taggant material is associated with indicia of the article that contain spatially encoded information.

12. A method as claimed in claim 11, wherein the indicia are a bar code.

13. A method as claimed in claim 11, wherein the indicia are a two-dimensional bar code.

14. A method as claimed in claim 11, wherein the indicia include letters and/or numbers.

15. A method as claimed in claim 11, wherein different taggant material is used at different regions of a label to further encode information.

* * * * *